United States Patent [19]

Nelson

[11] 4,061,965
[45] Dec. 6, 1977

[54] METHOD AND APPARATUS FOR MONITORING A CATHODICALLY PROTECTED CORRODIBLE HOLLOW MEMBER

[75] Inventor: Earnest E. Nelson, Woodbury Heights, N.J.

[73] Assignee: Mobil Oil Corporation, Dallas, Tex.

[21] Appl. No.: 689,161

[22] Filed: May 24, 1976

[51] Int. Cl.² .................. G01N 27/00; G01R 31/12; G01R 31/02
[52] U.S. Cl. .................................. 324/29; 204/148; 204/197; 324/52; 324/54; 324/71 R
[58] Field of Search ............ 324/3, 29, 1, 65 R, 324/65 CR, 71 R, 72, 67, 54, 52; 73/40.5 R; 204/147, 148, 196, 197, 195 C; 340/249

[56] References Cited
U.S. PATENT DOCUMENTS

| | | | |
|---|---|---|---|
| 2,803,797 | 8/1957 | Cowles | 324/29 |
| 2,893,939 | 7/1959 | Reid | 204/196 |
| 2,940,302 | 6/1960 | Scherbatskoy | 73/40.5 R |
| 3,055,970 | 9/1962 | Handley | 324/67 X |
| 3,064,127 | 11/1962 | Green et al. | 324/1 X |
| 3,284,789 | 11/1966 | Fisher | 340/249 |
| 3,754,275 | 8/1973 | Carter et al. | 324/67 X |
| 3,853,730 | 12/1974 | Anderson | 204/196 X |
| 3,878,453 | 4/1975 | Potter et al. | 324/67 X |

Primary Examiner—Gerard R. Strecker
Attorney, Agent, or Firm—Christensen, O'Connor, Garrison & Havelka

[57] ABSTRACT

A cathodic protection system for a buried, fluid pipeline that has an electrical lead or coil electrically coupled between the pipeline and a sacrificial anode. As the anode deteriorates by electrochemical reaction with its environment, a current flows through the lead or coil, producing an electromagnetic field that permeates the pipeline. The strength of this magnetic field can be correlated to the condition of the sacrificial anode and/or the condition of a protective coating on the pipeline. An apparatus for detecting the strength of the electromagnetic field travels through the pipeline in a scraper or similar device, senses the magnitude of the field, and generates a signal indicative of the condition of the cathodic protection system.

19 Claims, 3 Drawing Figures

METHOD AND APPARATUS FOR MONITORING A CATHODICALLY PROTECTED CORRODIBLE HOLLOW MEMBER

BACKGROUND OF THE INVENTION

This invention relates to cathodic protection systems for preventing corrosion of a metal structure, and more particularly, to a method and apparatus for remotely determining the functional condition of a cathodic protection system.

Cathodic protection systems are employed to prevent corrosion of metal structures exposed to an electrolytic environment. Cathodic protection can be effected for submarine or subterranean corrodible structures by electrically connecting the corrodible structure to sacrificial anodes constructed of a metal that is higher in the electromotive series than the protected structure, i.e., a metal that is anodic to the material of the protected structure. When the protected structure and the electrically connected sacrificial anode are both disposed within the same electrolytic environment (e.g., earth or water containing free positive ions), a galvanic cell is formed in which the protected structure is the cathode.

Metal atoms on the exposed surface of the sacrificial anode are ionized by the surrounding electrolyte and go into solution with the electrolyte, thereby corroding the sacrificial anode. Due to the difference in electrical potential between the cathodically protected metal and the sacrificial anode, electrons produced by the electrochemical corrosion reaction of the anode flow as an electrical current through the electrical connection between the sacrificial anode and the protected structure. When the electrons reach the protected structure, they either combine with positive ions in the electrolyte at the surface of the protected structure, or flow back to the sacrificial anode through the electrolyte to complete a current path between the sacrificial anode and the protected structure. The protected structure does not corrode since free electrons are readily available at the surface of that structure to chemically reduce or neutralize positive ions that reach the surface of the protected structure, which positive ions would otherwise initiate a corrosion reaction at the surface of the protected structure.

Often, the function of a cathodic protection system is supplemented by applying a protective coating to the exterior of the cathodically protected structures to reduce the exposure of the protected structure to the electrolyte environment. However, a protective coating will not completely isolate the protected structure from the electrolyte since small cracks or discontinuities in the coating develop as the coating ages, allowing the portion of the structure exposed through the cracks to be corroded. Further, such a coating is incapable of perfectly isolating the corrodible structure from positive ions in the surrounding electrolyte as some of the positive ions are capable of diffusion or migration through the protective coating itself.

Cathodic protection systems are capable of protecting the corrodible structure from corrosion as long as a sufficient amount of sacrificial anode remains to supply electrons to the protected structure. When an anode is nearly completely corroded, it must be replaced in order for the cathodic protection system to continue its function. The corrosion rate of the sacrificial anode, and thus the point in time when the anode needs to be replaced, is difficult to predict since it is influenced by a number of variable factors such as the composition of the surrounding soil or water and localized variations in that composition.

Although the prior art has devised a number of schemes for determining the condition of a cathodic protection system to ascertain whether the system is functioning, and/or for determining when the sacrificial anodes are in need of replacement, these schemes have proven unsatisfactory in certain applications. For example, in order to cathodically protect a considerable length of subterranean or submarine conduit or pipe, it is necessary to provide either a plurality of sacrificial anodes electrically connected to the pipe and spaced along the length of the pipe, or to provide a continuous sacrificial anode disposed along the length of the pipe having a plurality of electrical connections between the anode and the pipe with the electrical connections spaced along the pipe length. The condition of such a cathodic protection system is conventionally monitored by determining the polarity and/or magnitude of the electrical potential of the sacrificial anode and/or the electrical potential of the protected pipe with respect to a reference half-cell disposed in the electrolytic media surrounding the pipe. These determinations must be made at a plurality of locations along the length of the pipe to determine the condition of the entire system. To facilitate the monitoring tests, electrical connections, in the form of an insulated electrical conductor electrically connected to the sacrificial anode and/or the cathodically protected structure and routed to the surface of the electrolyte in which the system is disposed, are provided at various points along the pipe, e.g. at each connection between a sacrificial anode and the cathodically protected pipe.

Such prior art systems may be satisfactory under certain conditions. However, the installation and maintenance of the additional electrical connections between the anode and/or pipe and the surface of the electrolyte are expensive. Further, such monitoring techniques generally require a periodic manual test at each of the test locations to determine the local conditions of the protection system at various points along the length of the pipe, requiring maintenance personnel to traverse the pipeline route. In addition, pipelines that are routed over rough or mountainous terrain or under water are not readily accessible by maintenance personnel. Moreover, during inclement weather or during certain seasons of the year in northern areas of the country, it may be physically impossible to traverse the pipeline route and make the necessary measurements at all the test locations.

Accordingly, it is a broad object of this invention to provide apparatus and methods for monitoring the condition of a cathodic protection system for a length of corrodible structure such as a pipe or conduit that require neither electrical connections to the surface of the electrolyte nor manual tests at each connection between the sacrificial anodes and the protected structure to determine the condition of the system. It is a further object of this invention to provide methods and apparatus for remotely determining the condition of a cathodic protection system.

SUMMARY OF THE INVENTION

These and other objects are achieved in accordance with this invention by a cathodic protection system including at least one sacrificial anode for a length of metallic structure having an interior channel. The electrical connections between the sacrificial anode and the protected structure are arranged to establish electromagnetic fields that penetrate into the interior region of the protected structure as electrons flow between the sacrificial anode and the protected structure. The electromagnetic field within the interior of the protected structure is proportional to the current flowing through the electrical connection and is detected by apparatus that travels through the interior channel of the protected structure. The detection apparatus includes circuitry for supplying an electrical signal representative of the electromagnetic field at each connection between the protected structure and sacrificial anode. These electrical signals can either be recorded for later analysis at a convenient central location or telemetered to the central location as the electromagnetic fields are detected.

The electromagnetic field is indicative of two important system conditions. First, as the sacrificial anodes corrode, less anode surface area is exposed to the electrolytic environment and fewer free electrons are available to keep the protected structure from corroding. Since there are fewer free electrons available, the electrical current flowing between the anode and the protected structure decreases. In accordance with this invention, the decreased current flow results in a lower electromagnetic field strength within the interior channel of the protected structure. As the detected electromagnetic field is proportional to the remaining exposed surface area of the sacrificial anode, the electromagnetic field can be utilized to determine when the sacrificial anode should be replaced.

Secondly, in cathodically protected systems that include a protective coating applied to the exterior surface of the protected structure to impede corrosion, the detected electromagnetic field can be employed to provide an indication of undesirable changes in the condition of the protective coating such as the development of cracks in the protective coating. Such protective coating failures expose a greater surface area of the protected structure to the electrolyte with an attendant increase in the number of free electrons utilized to chemically reduce electrolyte ions reaching the exposed surface. Since these free electrons are supplied by the sacrificial anode, the electrical current through the conductor connecting the sacrificial anode increases with a corresponding detectable increase in the electromagnetic field within the interior region of the protected structure.

In one embodiment of the invention, the electrical connections between sacrificial anodes and a protected pipe of a pipeline system are arranged as electrical coils that are mounted in close proximity with the exterior walls of the protected pipe to supply an electromagnetic field that penetrates the pipe walls. The electromagnetic field produced by the coils is detected by appropriate circuitry included within a scraper or pig that is periodically sent through the pipe to perform functions such as cleaning the interior surface of the pipe. Signals proportional to each detected electromagnetic field are recorded by a suitable recording apparatus to permit analysis of the system condition at a convenient central location.

DETAILED DESCRIPTION

Figure 1:
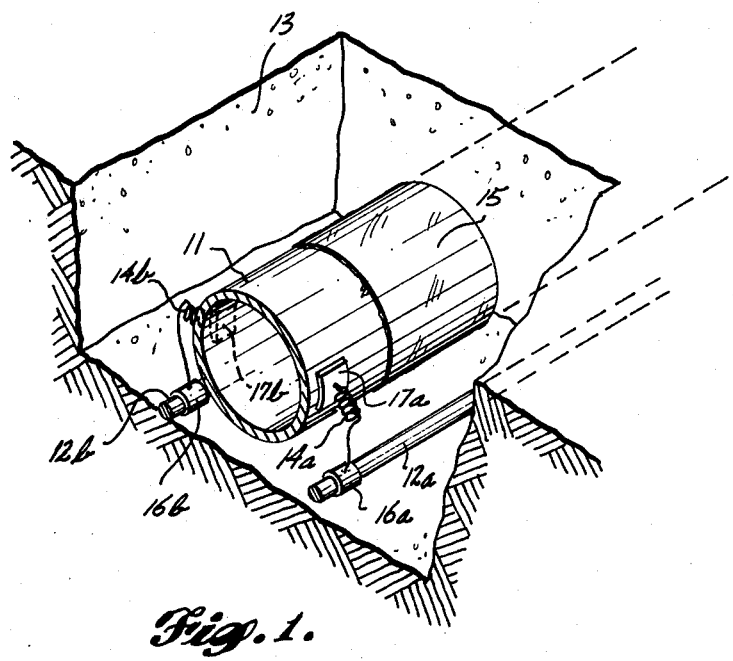
FIG. 1 is an isometric view depicting a section of a buried cathodically protected pipe in accordance with this invention.

Referring to FIG. 1, pipe 11 and sacrificial anodes 12a and 12b are each disposed in a backfilled ditch 13. The two sacrificial anodes 12a and 12b ae rod-like members placed in the ditch 13 on each side of the pipe 11 and oriented substantially parallel to pipe 11. It will be understood by those skilled in the art that multiple anodic members such as sacrificial anodes 12a and 12b are usually employed in installations in which pipe 11 is of large diameter to ensure that the entire surface of pipe 11 behaves as the cathode of a galvanic cell. Although this invention may be practiced in cathodic protection systems that employ a continuous anodic member electrically connected to pipe 11 at any number of points along the path of pipe 11, the invention can also be practiced in installations in which a plurality of separate anodic elements are disposed along the path of pipe 11 with each anodic element being electrically connected to the wall of pipe 11.

The sacrificial anodes 12a and 12b are electrically connected to the pipe 11 by electrically insulated conductors 14a and 14b that are formed or wound in the shape of a solenoidal coil. Conductors 14a and 14b are electrically connected to sacrificial anodes 12a and 12b by conventional means, for example, connecting collar 16a securely fastens conductor 14a to sacrificial anode 12a and provides electrical connection between the two elements. Similarly, the other end of conductors 14a and 14b are electrically connected to the exterior surface of pipe 11 by conventional means, for example, coupling plate 17a both mechanically and electrically interconnecting conductor 14a with pipe 11. In installations in which pipe 11 traverses long distances, electrical connections such as depicted by conductors 14a and 14b are generally located at predetermined intervals along the path of pipe 11 in order to maintain the full expanse as an electrical cathode of one or more galvanic cells. The distance between electrical interconnections in such an installation will vary, but will often be on the order of a few hundred feet.

Generally the exterior surface of pipe 11 is coated with a nonconductive material 15 that is relatively resistant to moisture penetration, including penetration by weak alkaline and acidic solutions. Such a nonconductive coating of itself impedes corrosion of pipe 11 since it effectively isolates the pipe surface from positive ions within the surrounding earth fill. Suitable nonconductive coatings are well known in the art, often having resistivities on the order of 100,000 ohms per square foot.

In a cathodically protected pipeline employing such a protective coating, the electrical current flowing through each conductor, such as conductor 14a of FIG. 1, supplies electrons to chemically reduce the positive ions reaching the metal surface of pipe 11 through discontinuities in the protective surface or by diffusion through the protective coating. In any given circumstances a specific current will flow through each conductor while the cathodic protection system is functioning normally. Although the exact magnitude of this current will be determined by such parameters as the electromotive potentials of the materials employed and the composition and moisture condition of the earth in that particular locality, the proper current magnitude at any or all connecting locations may be reliably estimated or measured upon initial installation of the system. Significant changes in the electrical current through a particular conductor evidence two types of problems within the cathodic protection system. First, should protective coating 15 fail, allowing areas of pipe 11 to be exposed to a greater number of positive electrolyte ions, the current will increase as more electrons flow through conductor 14 from sacrificial anode 12 to pipe 11. Secondly, as the sacrificial anode corrodes away, its surface area is reduced and fewer free electrons are produced by oxidation of sacrificial anode metal ions. With fewer electrons available, the current flow through conductor 14 decreases, and when a sufficient number of electrons are not available at pipe 11 to chemically reduce the positive electrolyte ions, pipe 11 begins to corrode.

In accordance with this invention, the current flow through the connection between the sacrificial anode and the protected pipe establishes a detectable electromagnetic field within the interior of the protected pipe. In the embodiment of this invention depicted in FIGS. 1 and 2, this electromagnetic field is established by coil-wound conductors 14a and 14b, which are mounted in close proximity with pipe 11 with the longitudinal axis of the coil intersecting the pipe wall. The current flow through such a solenoidal coil establishes an electromagnetic field having a magnetic induction or field strength directly proportional to the number of turns, the magnetic permeability of the coil core material, if any, and the current through the coil. As depicted in FIG. 3, the electromagnetic field established by the coil-wound conductor penetrates the walls of pipe 11 with the magnetic lines of force, denoted by dashed lines 24 of FIG. 3, following a closed path that extends through the core region of coil-wound conductor 14. Although the walls of pipe 11 may attenuate the electromagnetic field, with the attendant production of electrical eddy currents within the pipe walls, a detectable electromagnetic field is established in the interior region of pipe 11 directly adjacent to the electrical coil formed by conductor 14.

In accordance with this invention, the electromagnetic fields are detected by traveling module 21, of FIG. 3, which travels through the interior bore of pipe 11. Traveling module 21 is an enclosed, hollow structure that can be propelled through pipe 11 by propulsion means such as a battery-operated electrical motor, or in the case of a pipe that carries a fluid, can be urged through pipe 11 by the flowing fluid. Electromagnetic detectors 23a and 23b are mounted on the exterior of traveling module 21 so as to be in close proximity with the walls of pipe 11. As traveling module 21 passes through pipe 11, detectors 23a and 23b pass through the electromagnetic fields supplied by each coil wound conductor, thereby inducing a current in the detectors. Detectors 23a and 23b are electrically connected to input terminals of detector circuit 26, which is mounted within the interior of traveling module 21. As shall be discussed in greater detail hereinafter, detector circuit 26 contains conventional electronic circuitry, e.g. amplifiers, for processing the signals supplied by detectors 23a and 23b. The output terminal of detector circuit 26 is connected to instrumentation unit 27, which includes conventional circuitry for recording the signals supplied by detector circuit 26 or relaying the signals to any convenient location, such as the terminus of pipe 11.

Detectors 23a and 23b may be any conventional electromagnetic detection elements. Such detection units effectively function as an antenna to supply an electrical current that is proportional to the magnitude of each electromagnetic field through which the detection units pass. As will be recognized by those skilled in the art, a multitude of detector arrangements are suitable for the practice of this invention including a simple conductive probe passing through the wall of traveling module 21, or any number of more complex electrical coil configurations that can be mounted on the exterior of traveling module 21. The selection of a particular detector for use in this invention is usually determined by the sensitivity of the remaining portions of the electromagnetic detection system and the electromagnetic field produced in any given installation. As can be noted in FIG. 3, detector 23a can be located closer to the forward end of module 21 than the location of detector 23b. In installations in which pipeline 11 is electrically connected to sacrificial anodes 12a and 12b at diametrically opposed positions of a particular pipe cross-section, this orientation generates a distinct electrical current in each of the two detectors 23a and 23b as traveling module 21 passes by coil wound conductors 14a and 14b. That is, as module 21 passes along the interior of pipe 11, the forward detector 23a first cuts through the electromagnetic field supplied by coil-wound conductor 14a, resulting in an induced current in detector 23a. As traveling module 21 continues along pipe 11, the rear detector 23b then cuts through the electromagnetic field supplied by coil-wound conductor 14b, resulting in an induced current in detector 23b. Accordingly, two separate electrical signals are supplied to detector circuit 26 with the first signal being proportional to the current flowing through conductor 14a and the second signal being proportional to the current flowing through conductor 14b. Alternatively, two separate signals to represent the current flow through conductors 14a and 14b can be supplied by installing conductors 14a and 14b such that they are spaced from one another with respect to the longitudinal dimension of pipe 11. In such an installation, a single detector may be utilized in place of detectors 23a and 23b and separate electrical signals are produced as the single detector passes each coil-wound conductor. Such an embodiment may be especially advantageous in instances in which traveling module 21 rotates about its axis or does not maintain a predetermined orientation as it moves through pipe 11, thus necessitating electromagnetic detectors that will pass through the electromagnetic field regardless of the rotational orientation of module 21. Such detectors may be realized for example, by a plurality or array of single detectors mounted circumferentially around the periphery of module 21 or may be realized by a single or multiple turn conductive loop positioned around the periphery of module 21.

In any case, detector circuit 26 of FIG. 3 is electrically connected to electromagnetic detector units 23a and 23b and receives electrical signals proportional to the current through conductors 14a and 14b. Detector circuit 26 operates on the signal supplied by the electromagnetic detectors to provide an electrical signal compatible with instrumentation unit 27. Various conventional implementations of detector circuit 26 and instrumentation unit 27 can be utilized to suit the requirements of a particular installation. For example, instrumentation unit 27 can be a conventional recorder that stores electrical signals representative of the current flow through each connection between sacrificial anodes 12a and 12b and pipe 11. In such an embodiment, detector circuit 26 will generally include conventional circuitry for amplifying the signal provided by detectors 23 and, if the signal is to be recorded in a digital format, may include conventional analog-to-digital converter circuitry. On the other hand, in some installations it may be necessary or desirable to transmit the measured electromagnetic data to a central location as it is detected. In such cases instrumentation unit 27 can be any conventional transmission device ranging from a simple telephone circuit in the inspection of short pipelines where traveling module 21 is linked to one end of the pipe by a conductor, to more complex communication systems in which the detected electromagnetic signals are transmitted to a central location via a modulated RF, acoustic or light signal. In any case, it will be realized that detector circuit 26 and instrumentation unit 27 either store the electrical signal provided by detectors 23 on location within the traveling module 21 for later processing and analysis at a convenient remote location, when traveling module 21 is removed from the pipe 11, or detector circuit 26 and instrumentation unit 27 relay information to a remote location as traveling module 21 traverses through pipe 11.

In many pipeline systems, scrapers, commonly known as pigs, are utilized to travel through the pipe primarily for the purpose of cleaning the interior surfaces of the pipe wall. Pigs are conventionally constructed with peripheral seals to the pipe wall so as to form a movable plug within the pipe and are urged through the pipe by the fluid flow. Advantageously, the electromagnetic detection apparatus employed in the practice of this invention (i.e., detectors 23a and 23b, Detector circuit 26, and instrumentation unit 27) can be conveniently mounted within an existing pig modified to carry the detection apparatus or mounted within a pig specially constructed to serve as a detection apparatus carrier.

Regardless of whether the signals representative of the electromagnetic field at the location of each coil wound conductor 14 are stored within the instrumentation unit 27 or relayed immediately to a remote location for processing, it can be realized that as traveling module 21 traverses pipe 11 a plurality of signals are made available to indicate the condition of the protective anode 12 and/or the protective coating 15 over the entire expanse of pipe 11. These signals are correlated to specific locations along pipe 11 either by a priori knowledge of the location of each coil wound conductor 14 or by conventional distance measuring apparatus that can be included in instrumentation unit 27. Alternatively, in an embodiment in which traveling module 21 traverses pipe 11 with a constant or known velocity, the time intervals between successive detector signals can be utilized to identify a particular signal with a particular location along the pipe. Accordingly, the signals can be utilized to rather accurately determine the location of portions of the protective anode 12 that are in need of replacement and/or the location of portions of the pipe 11 where it is necessary to repair the protective coating 15.

Further, in accordance with this invention, variations in the condition of the protective coating 15 along the length of pipe 11 can be ascertained by comparing the successive detector signals. Such a comparison can provide an indication of impending failure of a region of protective coating prior to the time at which the failure reaches proportions that can be indicated by the signal supplied by a single coil wound conductor. That is, since in most installations the coil wound conductors are located within a few hundred feet of one another, conditions such as the moisture content of the surrounding electrolyte are generally fairly constant relative to adjacent coil wound conductors, with changes in the electromagnetic field caused by such conditions occurring rather gradually relative to the full expanse of the pipe 11. Thus, by comparing successive signals with one another, small changes in the condition of the protective coating 15 that may eventually result in more serious failure at a time when repair is difficult due to inclement weather can be detected and repaired during routine pipeline maintenance.

In a somewhat similar manner, the signals supplied during a particular traversal of the pipe 11 by traveling module 21 can be compared with the respective signals obtained during a previous traversal to monitor the rate at which the anodes 12 are deteriorating and/or monitor changes in the condition of the protective coating 15. For example, each signal obtained during a particular system monitoring operation in which traveling module 21 traverses the pipe 11 can be compared to the corresponding signal obtained during a previous system monitoring operation that may have been performed a matter of months before. The differences between the corresponding signals indicate the changes in the operation of the cathodic protection system during the time interval between the monitoring operations and hence indicate the rate of deterioration of the protective anodes and/or the protective coating.

In some situations it may be desirable or necessary to monitor the condition of the cathodic protection system in terms of the pipe-to-electrolyte voltage rather than in terms of the current flow from the sacrifical anode. In installations in which the electrolytic environment encompassing pipe 11 and protective anode 12 is such that the electric potential of the anode remains constant (either because of natural soil conditions or a chemical backfill such as calcium sulphate), the electrical potential between the pipe 11 and the surrounding electrolyte, e.g. the surrounding earth fill, can be rather accurately determined. The pipe to electrolyte potential is ascertainable since each detected electromagnetic field is porportional to the current flowing through the corresponding coil wound conductor 14 and the electrical resistance of each coil wound conductor 14 is ascertainable either by measurement thereof during the construction of the cathodic protection system or by mathematical calculation based on the coil configuration. More specifically, the pipe-to-anode potential can be expressed as $KF_aR_a$ where K is a constant of proportionality that is determined by the relationship between the current through a coil-wound conductor 14 and the electromagnetic field produced in the interior of pipe 11, $F_a$ is the detected electromagnetic field at the location of the "$a^{th}$" coil wound conductor 14, and $R_a$ is the electrical resistance of the "$a^{th}$" coil wound conductor 14. Thus the monitored electromagnetic fields can be directly correlated to the electrical potential between the pipe 11 and the anode 12 at each location of the coil wound conductor. Since the anode potential is constant and of a known or ascertainable magnitude, the pipe-to-electrolyte potential along the length of the pipe can be determined by subtracting the pipe-to-anode potential at each coil-wound conductor 14 from the anode potential.

Figure 2:
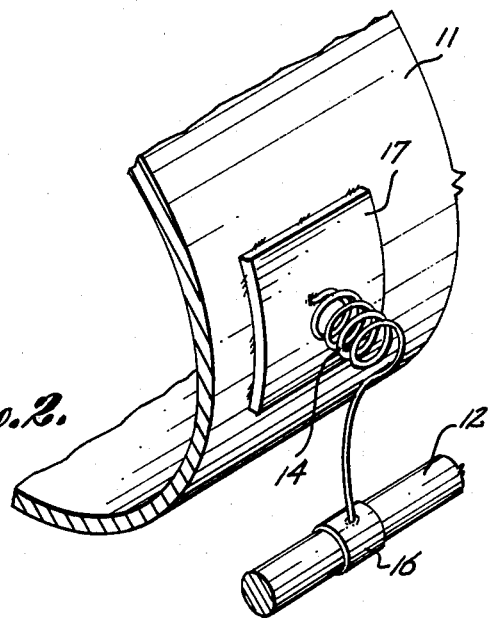
FIG. 2 is an isometric view of a portion of the cathodically protected pipe of the embodiment of FIG. 1 to depict an electrical connection between a sacrificial anode and a portion of a cathodically protected pipe in accordance with this invention.
Figure 3:
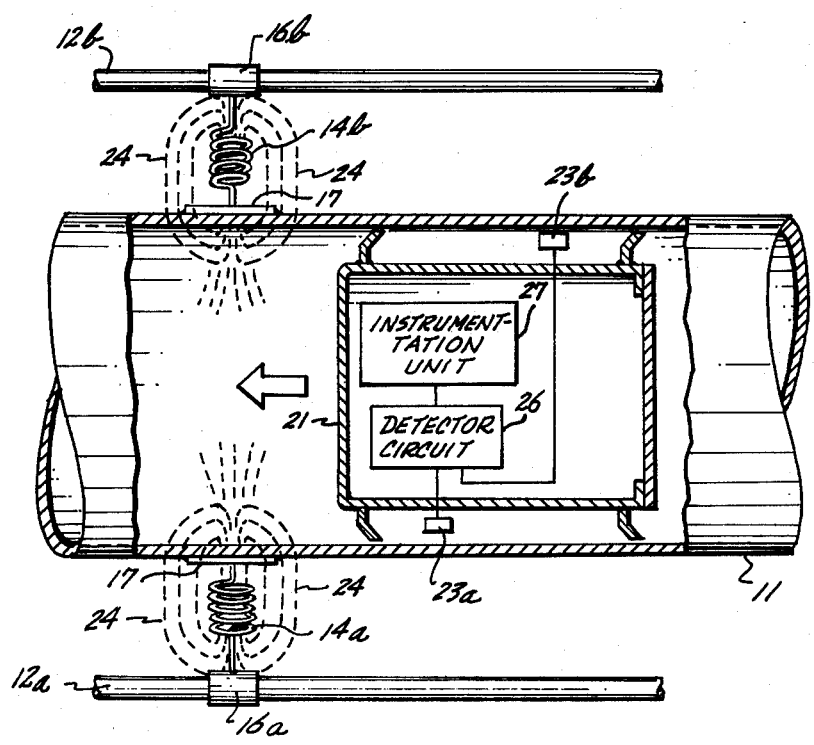
FIG. 3 is a plan view in partial longitudinal section of a portion of a cathodically protected pipe that illustrates a detection device traveling through the pipe to detect the electromagnetic fields established in accordance with this invention.

The disclosed embodiment of this invention depicted in FIGS. 1, 2 and 3 is intended to be exemplary and variations are possible without departing from the broad scope and spirit of this invention. It is especially important to realize that a variety of electrical coils other than solenoid coils 14a and 14b of the depicted embodiment may be satisfactorily employed in the practice of this invention. For example, a toroidially-wound coil can be utilized and oriented with respect to pipe 11 such that a detectable electromagnetic field is created in the interior of pipe 11. Further, it should be recognized that core material of relatively high magnetic permeability may be included within any coil used in the practice of this invention to concentrate and control the electromagnetic field produced by the electrical coil. In some installations it is also possible to eliminate separate electromagnetic detector units such as detectors 23a and 23b of FIG. 3. For example, in installations in which a substantial electromagnetic field is produced at each connection between sacrificial anode 12 and pipe 11, at least a portion of the walls of traveling module 21 can be constructed of, or surrounded by, electrically-conducting material. As traveling module 21 traverses each electromagnetic field, electrical eddy currents will be produced within the conductive material. Since the eddy currents are proportional to the current flowing in the cathodic connection, the magnitude of the eddy currents can then be detected by conventional circuit techniques and an appropriate electrical signal coupled to detector circuit 26 and instrumentation unit 27. Further, although the present invention has been described as used in a pipeline system, the invention can be practiced in conjunction with any cathodically protected elongate metal member having a longitudinally extending channel through which an instrumented traveling module can traverse. It is therefore intended, in view of the foregoing disclosure, that the scope of protection sought by Letters Patent be limited only by the definition of the invention contained in the appended claims.

What is claimed is:

1. In a cathodic protection system for an elongate corrodible member routed through an electrolytic environment, said corrodible member having a longitudinally extending channel therethrough, said cathodic protection system including at least one sacrificial anode disposed within said electrolytic environment in spaced proximity to said elongate corrodible member, and connecting means for electrically connecting said sacrificial anode to said elongate corrodible member, an improved system for monitoring the condition of said cathodic protection system comprising:
    first means, responsive to electrical current flowing through said connecting means, for establishing an electromagnetic field within said channel of said corrodible member, said electromagnetic field being proportional to said electrical current flowing through said connecting means; and
    second means, positionable in said longitudinally extending channel of said corrodible member, for detecting the magnitude of said electromagnetic field established within said channel of said corrodible member and for supplying a signal representative of the magnitude of said electromagnetic field.

2. The monitoring system of claim 1 wherein said first means comprises an electrical coil, said coil being located in close proximity to the exterior of said corrodible member to establish said electromagnetic field within said channel.

3. The monitoring system of claim 1 further comprising:
    third means for transporting said second means through said channel, said second means detecting said electromagnetic field as said third means transports said second means within proximity of said electromagnetic field.

4. The monitoring system of claim 3 further comprising:
    fourth means carried by said third means for recording said signal representative of said electromagnetic field.

5. In a cathodic protection system including a cathodically protected corrodible member having an interior channel and at least one sacrifical metal anode, the improvement comprising:
    connection means electrically connected between said corrodible member and said anodes for establishing an electromagnetic field proportional to the current flow therethrough, said connection means being so positioned and oriented relative to said corrodible member as to cause said electromagnetic field to penetrate through said corrodible member into the interior channel thereof, and
    detection means for determining the field strength of said electromagnetic field in said interior channel, said detection means being positionable within said interior channel of said corrodible member.

6. The improvement of claim 5 wherein said connection means comprises:
    an electrical coil electrically connected between said corrodible member and said sacrificial anode.

7. The improvement of claim 6 further comprising:
    traveling means for transporting said detection means through the interior channel of said cathodically protected member.

8. The improvement of claim 6 wherein said detection means includes means for supplying an electrical signal representative of said electromagnetic field strength, and means for relaying said representative signal to a location remote from said detection means.

9. The improvement of claim 6 wherein said detection means includes means for supplying an electrical signal representative of said electromagnetic field strength and means for recording said electrical signal.

10. A cathodically protected pipeline system comprising:
    a length of corrodible pipe routed through an electrolytic environment;
    at least one electrically continuous metallic conductor having a higher electromotive potential than the material forming said pipe, said conductor being routed through said electrolytic environment in spaced relationship with said length of pipe;
    a plurality of electrical coils, each of said electrical coils electrically connecting said metallic conductor and said pipe at predetermined positions spaced along the length of said pipe, each of said electrical coils being so positioned and so oriented relative to said pipe so as to establish an electromagnetic field within the interior of said pipe at the particular location of said electrical coil, said electromagnetic field being proportional to the current flow through said coil between said pipe and said metallic conductor;

carrier means for traversing through the interior of said pipe, said carrier means being propelled by a fluid flowing through said pipe;

means carried by said carrier means for supplying a signal representative of the strength of the electromagnetic field established by each of said electrical coils as said carrier means traverses past each of said predetermined positions; and means carried by said carrier means for conveying each of said representative signals to a predetermined remote location.

11. The cathodically protected pipeline system of claim 10 wherein said means for supplying said signal representative of the strength of said electromagnetic field includes at least one electromagnetic detector means for supplying an electrical signal as said detector means travels through the electromagnetic field supplied by each of said electrical coils and circuit means responsive to said signal supplied by said detector means for supplying said signal representative of said strength of said electromagnetic field to said conveying means.

12. The cathodically protected pipeline system of claim 11 wherein said means for conveying each of said representative signals includes recording means carried by said carrier means, said recording means responsive to the electrical signal supplied by said circuit means as said electromagnetic detector means travels through said electromagnetic field established by each of said electrical coils.

13. The method of monitoring the condition of a cathodic protection system that includes a cathodically protected hollow corrodible member, at least one sacrificial anode, and at least one electrical connection between said corrodible member and said sacrificial anode comprising the steps of:

establishing an electromagnetic field in the interior of said hollow cathodically protected member that is proportional to the electrical current flowing through said electrical connection; and detecting the magnitude of said electromagnetic field within the interior region of said hollow member.

14. The method of claim 13 further comprising the steps of:

generating a signal representative of the magnitude of said electromagnetic field; and recording said representative signal.

15. The method of claim 13 wherein the potential between the pipeline and the surrounding electrolytic environment is monitored, said method further comprising the steps of:

determining the electrical potential between said pipe and said sacrificial anode from said detected electromagnetic field and the resistance characteristic of said electrical connections; and determining the pipeline-to-electrolytic potential by subtracting said potential between said pipeline and said sacrificial anode from the electrical potential of said sacrificial anode.

16. The method of claim 13, wherein said cathodic protection system includes a plurality of said electrical connections, each of said electrical connections being positioned at predetermined locations along the corrodible member, further comprising the step of comparing the detected magnitude of the electromagnetic field caused by a particular electrical connection with the magnitude of the electromagnetic field caused by at least one other of said electrical connections to determine the relative condition of said cathodic protection system adjacent respective ones of said electrical connections.

17. A method of monitoring the condition of a cathodic protection system for a fluid carrying pipeline, said system including a sacrificial anode and at least one electrical connection between said pipeline and said anode, comprising the steps of:

establishing an electromagnetic field at a predetermined location in the interior of said pipeline that is proportional to the electrical current flowing through said electrical connection;

conveying a device for detecting said electromagnetic field and generating a signal representative of the magnitude thereof through said pipeline; and generating a signal representative of the magnitude of said electromagnetic field as said device traverses past said predetermined location.

18. The method of claim 17 wherein said device is conveyed through said pipeline by:

positioning said device in a carrier sized to move through said pipeline;

inserting said carrier in said pipeline; and pumping a fluid through said pipeline to urge said carrier through said pipeline.

19. The method of claim 18 further comprising the steps of:

electrically coupling a signal recording apparatus to said device and positioning said signal recording apparatus in said carrier with said device; and recording said representative signal as it is generated.

* * * * *